(12) United States Patent
Zimmermann et al.

(10) Patent No.: US 8,410,090 B2
(45) Date of Patent: Apr. 2, 2013

(54) HETEROCYCLYLAMIDE-SUBSTITUTED THIAZOLES, PYRROLES AND THIOPHENES

(75) Inventors: Holger Zimmermann, Wuppertal (DE); David Brueckner, Weil am Rhein (DE); Kerstin Henninger, Wuppertal (DE); Martin Hendrix, Odenthal (DE); Martin Radtke, Erkrath (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 780 days.

(21) Appl. No.: 11/988,911

(22) PCT Filed: Jul. 1, 2006

(86) PCT No.: PCT/EP2006/006434
§ 371 (c)(1),
(2), (4) Date: Feb. 22, 2010

(87) PCT Pub. No.: WO2007/009578
PCT Pub. Date: Jan. 25, 2007

(65) Prior Publication Data
US 2010/0144752 A1    Jun. 10, 2010

(30) Foreign Application Priority Data
Jul. 15, 2005    (DE) .......................... 10 2005 033 103

(51) Int. Cl.
| | | |
|---|---|---|
| *A61P 31/12* | (2006.01) | |
| *A61K 31/38* | (2006.01) | |
| *A61K 31/40* | (2006.01) | |
| *C07D 401/12* | (2006.01) | |
| *C07D 409/12* | (2006.01) | |
| *C07D 417/12* | (2006.01) | |

(52) U.S. Cl. .............. 514/218; 514/252.13; 514/253.09; 514/253.1; 514/253.11; 514/254.01; 514/254.02; 540/575; 544/364; 544/369; 544/372; 544/379

(58) Field of Classification Search .................. 514/218, 514/252.13, 253.09, 253.1, 253.11, 254.01, 514/254.02; 540/575; 544/364, 369, 372, 544/379
See application file for complete search history.

(56) References Cited

U.S. PATENT DOCUMENTS

| 6,500,817 | B1 | 12/2002 | Fischer et al. |
| 7,132,463 | B2 | 11/2006 | Hwang et al. |
| 2005/0059658 | A1 | 3/2005 | Wunberg et al. |
| 2010/0048583 | A1* | 2/2010 | Leban et al. ............... 514/253.1 |

FOREIGN PATENT DOCUMENTS

| JP | 2002-539119 | 11/2002 |
| JP | 2004-530727 | 10/2004 |
| JP | 2006-509098 | 3/2006 |
| WO | WO-99/23091 | 5/1999 |
| WO | WO-2004/002481 | 1/2004 |
| WO | WO-2004/052852 | 6/2004 |

OTHER PUBLICATIONS

Burak et al., Pharmazie (1992) 47(7):492-495.
Chong et al., Abstracts of the 39th Interscience Conference on Antimicrobial Agents and Chemotherapy, (1999) p. 439.
Cinatl et al., FEMS Microbiology Reviews (2004) 28:59-77.
Hodgetts et al., Org. Lett. (2002) 4:1363-1366.
International Search Report for PCT/EP2006/006434, mailed on Oct. 17, 2006, 3 pages.
International Preliminary Report on Patentability for PCT/EP2006/006434, issued Jan. 29, 2008, 7 pages.
Kiryanov et al., Tetrahedron Lett. (2001) 42:8797-8800.
Kraemer et al., Cancer Research (1983) 43:4822-4827.
Okonya et al., Tetrahedron Lett. (2002) 43:7051-7054.

* cited by examiner

*Primary Examiner* — Brenda Coleman
(74) *Attorney, Agent, or Firm* — Morrison & Foerster LLP

(57) ABSTRACT

The invention relates to heterocyclylamide-substituted thiazoles, pyrroles and thiophenes and processes for their preparation, to pharmaceutical compositions containing them, and to their use for the treatment and/or prophylaxis of diseases, in particular for the use as antiviral agents, especially against cytomegaloviruses.

6 Claims, No Drawings

HETEROCYCLYLAMIDE-SUBSTITUTED THIAZOLES, PYRROLES AND THIOPHENES

The invention relates to heterocyclylamide-substituted thiazoles, pyrroles and thiophenes and processes for their preparation, to their use for the treatment and/or prophylaxis of diseases and to their use for preparing medicaments for the treatment and/or prophylaxis of diseases, in particular for the use as antiviral agents, especially against cytomegaloviruses.

WO 99/23091 describes aromatic heterocyclic compounds as antiinflammatory agents which, inter alia, may be suitable for the treatment of viral infections and WO 04/052852 describes 3-pyrrolylurea derivatives as antiviral agents which carry a carbocycle on the urea as a substituent.

Agents with antiviral activity and a different structure are available on the market; however, the therapies currently available with ganciclovir, valganciclovir, foscarnet and cidofovir are associated with severe side effects, for example nephrotoxicity, neutropenia or thrombocytopenia. In addition, it is always possible for resistance to develop. Novel agents for an effective therapy are therefore desirable.

One object of the present invention is therefore to provide novel compounds having the same or improved antiviral action for the treatment of viral infective diseases in humans and animals.

It has been found, surprisingly, that the substituted heterocycles described in the present invention have high antiviral activity.

The present invention provides compounds of the formula

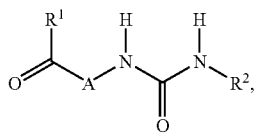

(I)

in which
$R^1$ represents a group of the formula

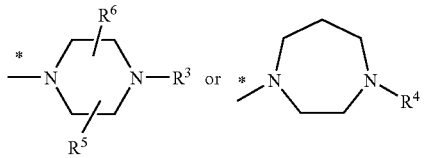

where
\* represents the point of attachment to the carbonyl group,
$R^3$ represents phenyl or 5- or 6-membered heteroaryl,
  where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
$R^4$ represents phenyl or 5- or 6-membered heteroaryl,
  where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and
$R^5$ and $R^6$ independently of one another represent hydrogen, methyl or ethyl,
$R^2$ represents phenyl,
  where phenyl may be substituted by 1 to 3 substituents, where the substituents independently of one another are selected from the group consisting of halogen, hydroxyl, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy,
A represents a group of the formula

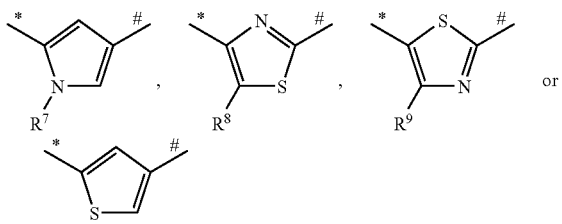

where
\* represents the point of attachment to the carbonyl group,
\# represents the point of attachment to the nitrogen atom of the urea,
$R^7$ represents $C_1$-$C_6$-alkyl,
  where alkyl may be substituted by one substituent, where the substituent is selected from the group consisting of $C_3$-$C_6$-cycloalkyl, $C_6$-$C_{10}$-aryl and 5- or 6-membered heteroaryl,
  where cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and
$R^8$ and $R^9$ independently of one another represent hydrogen, halogen or $C_1$-$C_6$-alkyl,
  where alkyl may be substituted by one substituent, where the substituent is selected from the group consisting of $C_3$-$C_6$-cycloalkyl, $C_6$-$C_{10}$-aryl and 5- or 6-membered heteroaryl,
    in which cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and their salts, their solvates and the solvates of their salts.

Compounds according to the invention are the compounds of the formula (I) and their salts, solvates and solvates of the salts; the compounds embraced by formula (I) of the formulae mentioned below and their salts, solvates and solvates of the salts and the compounds embraced by formula (I) and mentioned hereinbelow as exemplary embodiments and their salts, solvates and solvates of the salts, if the compounds mentioned hereinbelow, embraced by formula (I), are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can exist in tautomeric forms, the present invention comprises all tautomeric forms.

Salts in the context of the present invention are preferably physiologically acceptable salts of the compounds according to the invention. Also provided, however, are salts which for their part are not suitable for pharmaceutical applications but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium and potassium salts), alkaline earth metal salts (for example calcium and magnesium salts) and ammonium salts derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the present invention, solvates are those forms of the compounds according to the invention which form a complex in the solid or liquid state by coordination with solvent molecules. Hydrates are a special form of solvates in which the coordination takes place with water.

Moreover, the present invention also includes prodrugs of the compounds according to the invention. The term "prodrugs" embraces compounds which for their part may be biologically active or inactive but which, during their residence time in the body, are converted into compounds according to the invention (for example metabolically or hydrolytically).

In the context of the present invention, the substituents are, unless specified otherwise, as defined below:

Alkyl per se and "alk" and "alkyl" in alkoxy, alkylamino, alkoxycarbonyl and alkylaminocarbonyl represent a straight-chain or branched alkyl radical having generally 1 to 6 ("$C_1$-$C_6$-alkyl"), preferably 1 to 4, particularly preferably 1 to 3, carbon atoms, by way of example and by way of preference methyl, ethyl, n-propyl, isopropyl, tert-butyl, n-pentyl and n-hexyl.

Alkoxy represents, by way of example and by way of preference, methoxy, ethoxy, n-propoxy, isopropoxy, tert-butoxy, n-pentoxy and n-hexoxy.

Alkylamino represents an alkylamino radical having one or two alkyl substituents (chosen independently of one another), by way of example and by way of preference methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-iso-propyl-N-n-propylamino, N-t-butyl-N-methylamino, N-ethyl-N-n-pentylamino and N-n-hexyl-N-methylamino. $C_1$-$C_3$-Alkylamino represents, for example, a monoalkylamino radical having 1 to 3 carbon atoms or represents a dialkylamino radical having 1 to 3 carbon atoms each per alkyl substituent.

Alkoxycarbonyl represents, by way of example and by way of preference, methoxycarbonyl, ethoxy-carbonyl, n-propoxycarbonyl, isopropoxycarbonyl, tert-butoxycarbonyl, n-pentoxycarbonyl and n-hexoxycarbonyl.

Alkylaminocarbonyl represents an alkylaminocarbonyl radical having one or two alkyl substituents (chosen independently of one another), by way of example and by way of preference methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentyl-aminocarbonyl and N-n-hexyl-N-methylaminocarbonyl. $C_1$-$C_3$-Alkylaminocarbonyl represents, for example, a monoalkylaminocarbonyl radical having 1 to 3 carbon atoms or represents a dialkylamino-carbonyl radical having 1 to 3 carbon atoms each per alkyl substituent.

Aryl represents a mono- or bicyclic aromatic carbocyclic radical having generally 6 to 10 carbon atoms; by way of example and by way of preference phenyl and naphthyl.

In the context of the invention, 5- or 6-membered heteroaryl generally represents an aromatic monocyclic radical having 5 or 6 ring atoms and up to 4 heteroatoms from the group consisting of S, O and/or N. The heteroaryl radical may be attached via a carbon or a heteroatom. The following radicals may be mentioned by way of example and by way of preference: thienyl, furyl, pyrrolyl, thiazolyl, oxazolyl, pyrazolyl, imidazolyl, pyridyl, pyrimidyl and pyridazinyl.

Cycloalkyl represents a cycloalkyl group having generally 3 to 6 carbon atoms, by way of example and by way of preference cyclopropyl, cyclobutyl, cyclopentyl, cyclohexyl and cycloheptyl.

Halogen represents fluorine, chlorine, bromine and iodine.

In the context of the present invention, preference is given to compounds of the formula (I),
in which
$R^1$ represents a group of the formula

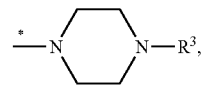

where
* represents the point of attachment to the carbonyl group,
$R^3$ represents phenyl or 5- or 6-membered heteroaryl,
where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoro-methoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^2$ represents phenyl,
where phenyl may be substituted by 1 to 3 substituents, where the substituents independently of one another are selected from the group consisting of halogen, hydroxyl, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy, A represents a group of the formula

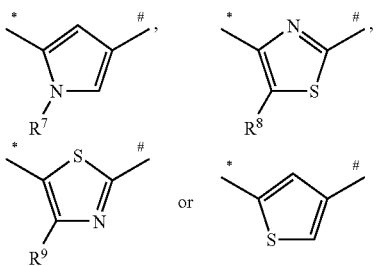

where
* represents the point of attachment to the carbonyl group,
# represents the point of attachment to the nitrogen atom of the urea, $R^7$ represents $C_1$-$C_6$-alkyl,
where alkyl may be substituted by one substituent, where the substituent is selected from the group consisting of $C_3$-$C_6$-cycloalkyl, $C_6$-$C_{10}$-aryl, and 5- or 6-membered heteroaryl,
where cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and
$R^8$ and $R^9$ represent, independently of one another, hydrogen, halogen or $C_1$-$C_6$-alkyl, and their salts, their solvates and the solvates of their salts.

In the context of the present invention, preference is also given to compounds of the formula (I),
in which
$R^1$ represents a group of the formula

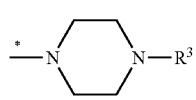

where
* represents the point of attachment to the carbonyl group,
$R^3$ represents phenyl or pyridyl,
where phenyl and pyridyl may be substituted by 1 to 3 substituents, where the substituents independently of one another are selected from the group consisting of halogen, nitro, cyano, trifluoromethyl, difluoromethyl, trifluoromethoxy, difluoro-methoxy, monofluoromethoxy, $C_1$-$C_4$-alkyl and $C_1$-$C_4$-alkoxy, $R^2$ represents phenyl,
where phenyl may be substituted by 1 to 3 substituents, where the substituents independently of one another are selected from the group consisting of fluorine, chlorine, trifluoromethoxy, difluoromethoxy, trifluoromethylthio and methyl, A represents a group of the formula

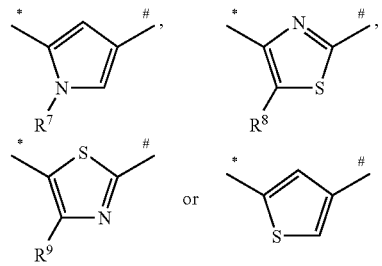

where
* represents the point of attachment to the carbonyl group,
# represents the point of attachment to the nitrogen atom of the urea, $R^7$ represents methyl, ethyl or n-butyl,
where methyl, ethyl and n-butyl may be substituted by one substituent, where the substituent is selected from the group consisting of cyclopropyl and phenyl,
where phenyl may be substituted by one trifluoromethyl substituent, and $R^8$ and $R^9$ represent, independently of one another, hydrogen, bromine, chlorine, methyl or ethyl,
and their salts, their solvates and the solvates of their salts.

In the context of the present invention, preference is also given to compounds of the formula (I) in which $R^1$ represents a group of the formula

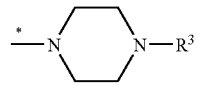

where
* represents the point of attachment to the carbonyl group, and
$R^3$ represents phenyl or pyridyl,
where phenyl and pyridyl may be substituted by 1 to 3 substituents, where the substituents independently of one another are selected from the group consisting of halogen, nitro, cyano, trifluoromethyl, difluoromethyl, trifluoromethoxy, difluoro-methoxy, monofluoromethoxy, $C_1$-$C_4$-alkyl and $C_1$-$C_4$-alkoxy.

In the context of the present invention, preference is also given to compounds of the formula (I) in which $R^2$ represents phenyl, where phenyl may be substituted by 1 to 3 substituents, where the substituents independently of one another are selected from the group consisting of fluorine, chlorine, trifluoromethoxy, difluoromethoxy, trifluoromethylthio and methyl.

In the context of the present invention, preference is also given to compounds of the formula (I), in which A represents a group of the formula

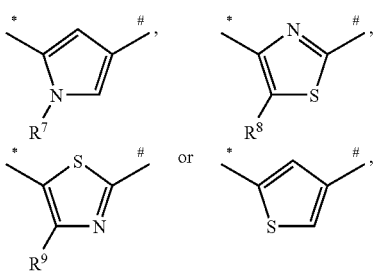

where
* represents the point of attachment to the carbonyl group,
# represents the point of attachment to the nitrogen atom of the urea,
$R^7$ represents methyl, ethyl or n-butyl,
where methyl, ethyl and n-butyl may be substituted by one substituent, where the substituent is selected from the group consisting of cyclopropyl and phenyl,
where phenyl may be substituted by one trifluoromethyl substituent,
$R^8$ represents hydrogen, bromine, chlorine or methyl, and
$R^9$ represents hydrogen.

The invention furthermore provides a process for preparing the compounds of the formula (I) where
according to process [A] a compound of the formula

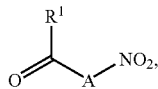 (II)

in which
$R^1$ is as defined above,
is reacted in the first step with a reducing agent and in the second step in the presence of a carbonic acid derivative with a compound of the formula $H_2N-R^2$ (III), in which
$R^2$ is as defined above,
or
according to process [B] a compound of the formula (II) is reacted in the first step with a reducing agent and in the second step with a compound of the formula $OCN-R^2$ (IV), in which
$R^2$ is as defined above,
or
according to process [C] a compound of the formula

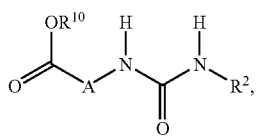 (V)

in which
$R^2$ is as defined above, and
$R^{10}$ represents methyl or ethyl,
is reacted in the first step with a base and in the second step with a compound of the formula $R^1-H$ (VI), in which
$R^1$ is as defined above, in the presence of dehydrating agents.

The compounds of the formulae (III), (IV) and (VI) are known or can be synthesized by known processes from the appropriate starting materials.

For processes [A] and [B], step 1, the following applies:
The reaction is generally carried out in inert solvents, preferably in a temperature range from 0° C. to the reflux of the solvents at atmospheric pressure to 3 bar.

Reducing agents are, for example, palladium-on-carbon and hydrogen, formic acid/triethylamine/palladium-on-carbon, zinc, zinc/hydrochloric acid, iron, iron/hydrochloric acid, iron(II) sulphate/hydrochloric acid, sodium sulphide, sodium disulphide, sodium dithionite, ammonium polysulphide, sodium borohydride/nickel chloride, tin dichloride, titanium trichloride or Raney nickel and aqueous hydrazine solution; preference is given to Raney nickel and aqueous hydrazine solution, palladium-on-carbon and hydrogen or formic acid/triethylamine/palladium-on-carbon.

Inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane, cyclohexane or mineral oil fractions, or other solvents, such as dimethylformamide, dimethylacetamide, acetonitrile or pyridine, in the case of water-miscible solvents also mixtures of the same with water; preferred solvents are methanol, ethanol, isopropanol and, in the case of Raney nickel and aqueous hydrazine solution, tetrahydrofuran.

For process [A], step 2, the following applies:
The reaction is generally carried out in inert solvents, preferably in a temperature range of from room temperature to 40° C. at atmospheric pressure.

Carbonic acid derivatives are, for example, N,N-carbonyldiimidazole, phosgene, diphosgene, triphosgene, phenyl chloroformate or 4-nitrophenyl chloroformate; preference is given to N,N-carbonyldiimidazole.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulphoxide, acetonitrile or pyridine, in the case of water-miscible solvents also mixtures of the same with water; preference is given to dimethyl sulphoxide.

For process [B], step 2, the following applies:
The reaction is generally carried out in inert solvents, if appropriate in the presence of a base, preferably in a temperature range of from room temperature to the reflux of the solvents at atmospheric pressure.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulphoxide, acetonitrile or pyridine; preference is given to tetrahydrofuran or methylene chloride.

Bases are, for example, alkali metal carbonates, such as caesium carbonate, sodium carbonate or potassium carbonate, or potassium tert-butoxide, or other bases, such as sodium hydride, DBU, triethylamine or diisopropylethylamine, preferably triethylamine.

For process [C], step 1, the following applies:

The reaction is generally carried out in inert solvents, preferably in a temperature range of from 0° C. to the reflux of the solvents at atmospheric pressure.

Bases are, for example, alkali metal hydroxides, such as sodium hydroxide, lithium hydroxide or potassium hydroxide, or alkali metal carbonates, such as caesium carbonate, sodium carbonate or potassium carbonate, preferably sodium hydroxide.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane, cyclohexane or mineral oil fractions, or other solvents, such as dimethylformamide, dimethylacetamide, dimethyl sulphoxide, acetonitrile or pyridine, or mixtures of solvents with water; the preferred solvent is a mixture of ethanol and water.

For process [C], step 2, the following applies:

The reaction is generally carried out in inert solvents, if appropriate in the presence of a base, preferably in a temperature range of from −70° C. to 40° C. at atmospheric pressure.

Dehydrating agents suitable for this purpose are, for example, carbodiimides, such as, for example, N,N'-diethyl-, N,N'-dipropyl-, N,N'-diisopropyl-, N,N'-dicyclohexylcarbodiimide, N-(3-dimethyl-aminoisopropyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium-3-sulphate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these, with bases.

Bases are, for example, alkali metal carbonates, such as, for example, sodium carbonate or potassium carbonate, or sodium bicarbonate or potassium bicarbonate, or organic bases, such as trialkylamines, for example triethylamine, N-methylmorpholine, N-methylpiperidine, 4-dimethyl-aminopyridine (DMAP) or diisopropylethylamine, or DBU, DBN, pyridine; preference is given to triethylamine.

The condensation is preferably carried out using TBTU and DMAP.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulphoxide, acetonitrile or pyridine, in the case of water-miscible solvents also mixtures of the same with water; preference is given to dimethylformamide.

In an alternative process, the carboxylic acids obtained from the first step of process [C], may first be reacted in the second step with a chlorinating reagent such as, for example, thionyl chloride to form carboxylic chloride and subsequently with compounds of the formula (VI) in the presence of a base to form compounds of the formula (I).

The compounds of the formula (II) are known or can be prepared by reacting compounds of the formula

(VII)

in which $R^{10}$ is as defined above, in the first step with a base and in the second step with compounds of the formula (VI), in the presence of dehydrating agents.

The reaction is carried out as described in process [C].

The compounds of the formula (VII) are known or can be prepared by reacting compounds of the formula

(VIII)

in which $R^{10}$ is as defined above, with fuming nitric acid, concentrated nitric acid, nitrating acid or other mixing ratios of sulphuric acid and nitric acid, if appropriate in acetic anhydride as solvent, preferably in a temperature range of from room temperature to 60° C. at atmospheric pressure.

The compounds of the formula (VIII) are known or can be prepared by known processes from the appropriate starting materials.

The compounds of the formula (V) are known or can be prepared by reacting compounds of the formula (VII) in the first step with a reducing agent and in the second step in the presence of a carbonic acid derivative with compounds of the formula (III) or in the second step with compounds of the formula (IV).

The reaction is carried out as described in processes [A] and [B].

Synthesis scheme 1:

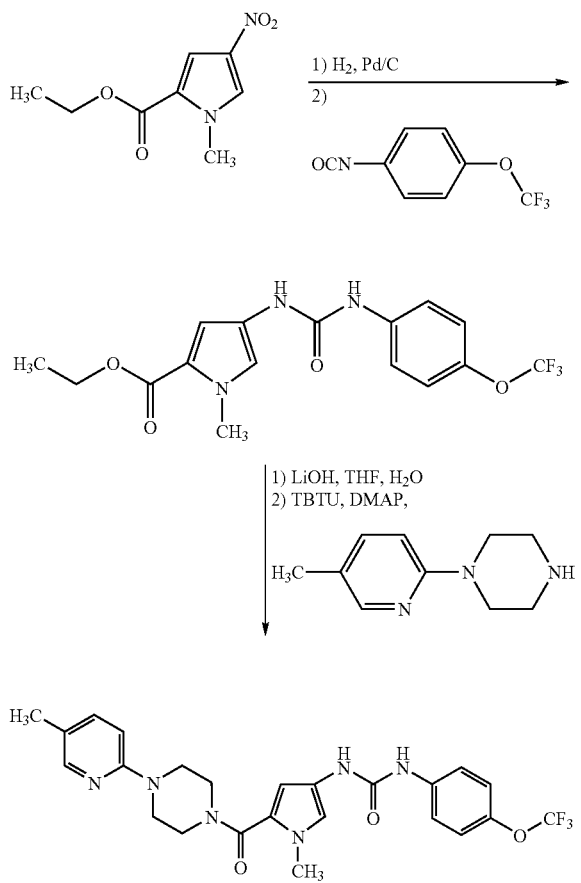

Synthesis scheme 2:

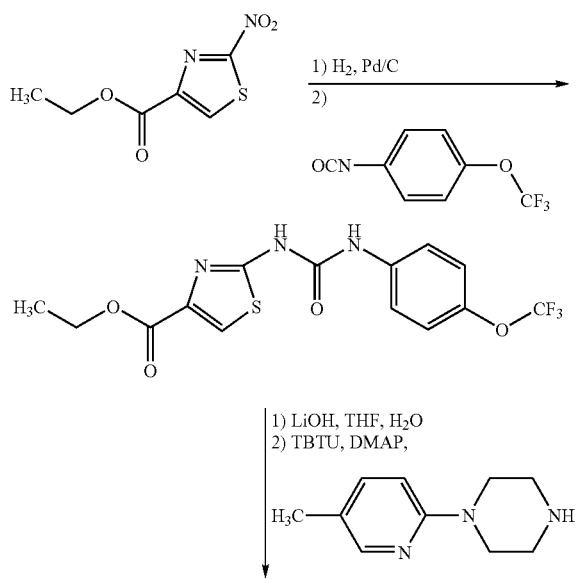

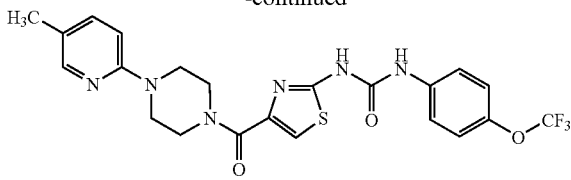

The compounds of the general formula (I) according to the invention show an unforeseeable, surprising activity spectrum. They have an antiviral effect on representatives of the group of the Herpes viridae (herpes viruses), especially on cytomegaloviruses (CMV), in particular on the human cytomegalovirus (HCMV). They are thus suitable for the treatment and prophylaxis of diseases, especially infections with viruses, in particular the viruses mentioned above, and the infective diseases caused thereby. Hereinbelow, a viral infection is to be understood as meaning both an infection with a virus and a disease caused by an infection with a virus.

By virtue of their particular properties, the compounds of the general formula (I) can be used for preparing medicaments suitable for the prophylaxis and/or treatment of diseases, in particular viral infections.

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplantation patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infections in immunosuppressed patients associated with cancer and cancer therapy.
6) Treatment of HCMV-positive cancer patients with the target to reduce HCMV-mediated tumour progression (cf. J. Cinatl, et al., *FEMS Microbiology Reviews* 2004, 28, 59-77).

The compounds according to the invention are preferably used for preparing medicaments suitable for the prophylaxis and/or treatment of infections with a representative of the group of the Herpes viridae, in particular a cytomegalovirus, especially the human cytomegalovirus.

By virtue of their pharmacological properties, the compounds according to the invention can be used alone and, if required, also in combination with other active compounds, in particular antiviral active compounds, such as, for example, gancyclovir, valganciclovir or acyclovir, for the treatment and/or prevention of viral infections, in particular HCMV infections.

The present invention furthermore provides the use of the compounds according to the invention for the treatment and/or prophylaxis of disorders, preferably of viral infections, in particular of infections with the human cytomegalovirus (HCMV) or another representative of the group of the Herpes viridae.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an antivirally effective amount of the compounds according to the invention.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, milk, pastes, foams, dusting powders, implants or stents.

The compounds according to the invention can be converted into the stated administration forms. This can take place in a manner known per se by mixing with inert nontoxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert nontoxic, pharmaceutically acceptable auxiliaries, and their use for the purposes mentioned above.

In general, it has proved advantageous to administer on intravenous administration amounts of from about 0.001 to 10 mg/kg, preferably from about 0.01 to 5 mg/kg, of body weight to achieve effective results, and the dosage on oral administration is from about 0.01 to 25 mg/kg, preferably from 0.1 to 10 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations used:
BINAP 2,2'-Bis(diphenylphosphino)-1,1'-binaphthyl
Ex. Example
$CD_3CN$ Deuteroacetonitrile
TLC Thin-layer chromatography
DCI Direct chemical ionization (in MS)
DCM Dichloromethane
DMA N,N-Diisopropylethylamine (Hünig base)
DMAP 4-N,N-Dimethylaminopyridine
DMF N,N-Dimethylformamide
DMSO Dimethyl sulphoxide
EDCI×HCl N'-(3-Dimethylaminopropyl)-N-ethylcarbodiimide hydrochloride
EA Ethyl acetate
EI Electron impact ionization (in MS)
ESI Electrospray ionization (in MS)
m.p. Melting point
sat. Saturated
h Hour
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HPLC High pressure, high performance liquid chromatography
conc. Concentrated
LC-MS Liquid chromatography-coupled mass spectroscopy
LDA Lithium diisopropylamide
lit. Literature (reference)
sol. Solution
MS Mass spectroscopy
NMR Nuclear magnetic resonance spectroscopy
RP-HPLC Reverse phase HPLC
RT Room temperature
$R_t$ Retention time (in HPLC)
TBTU O-(Benzotriazol-1-yl)-N,N,N',N'-tetramethyluronium tetrafluoroborate
THF Tetrahydrofuran
dil. Dilute
aqu. Aqueous HPLC and LC-MS Methods:

Method 1 (LC-MS): MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2 (LC-MS): Instrument: Micromass Quattro LCZ with HPLC Agilent series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 3 (LC-MS): MS instrument type: Micromass ZQ; HPLC instrument type: HP 1100 series; UV DAD; column: Phenomenex Synergi 2 μHydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Starting Materials

Example 1A

1-Methyl-2-trichloroacetyl-1H-pyrrole

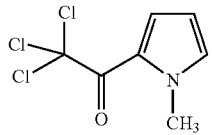

Under argon, 1.09 ml (12.3 mmol) of trichloroacetyl chloride are initially charged in 5 ml of DCM, and a solution of N-methylimidazole and 3 ml of DCM is added dropwise at RT over a period of 30 min. The reaction solution is allowed to stir at RT overnight and then concentrated, and the residue is purified over a flash frit (cyclohexane, cyclohexane/ethyl acetate 40:1). This gives the product as a liquid.

Yield: 2.12 g (76% of theory)

LC-MS (Method 1): $R_t$=2.34 min.; MS (EI$^+$): m/z=225 (M$^+$)

Example 2A

1-Methyl-4-nitro-2-trichloroacetyl-1H-pyrrole

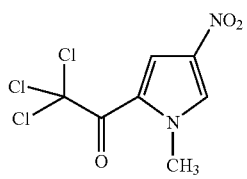

2.12 g (9.34 mmol) of 1-methyl-2-trichloroacetyl-1H-pyrrole are dissolved in 9.5 ml of acetic anhydride and cooled to −20° C., and 0.43 ml (9.34 mmol) of nitric acid is added. The mixture is slowly warmed to RT and stirred at RT for 1 h. The reaction mixture is poured into 95 g of ice and stirred vigorously for 2.5 h (initially oily deposit then crystallization). The precipitate is filtered off with suction, triturated with 20 ml of methanol, filtered and dried under reduced pressure overnight. To remove the regioisomers, which are also formed, the product is triturated with 10 ml of acetic acid/water 1:1 for 2 h, and the solid is filtered off with suction and dried under reduced pressure. This gives a solid.

Yield: 1.71 g (67% of theory)

LC-MS (Method 2): $R_t$=2.51 min.

$^1$H-NMR (400 MHz, DMSO-d$_6$): δ=8.58 (d, 1H), 7.80 (d, 1H), 4.00 (s, 3H).

Example 3A

Ethyl 1-methyl-4-nitro-1H-pyrrole-2-carboxylate

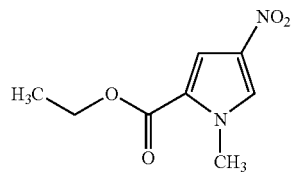

0.50 g (1.84 mmol) of 1-methyl-4-nitro-2-trichloroacetyl-1H-pyrrole are initially charged in 5 ml of ethanol, 0.26 ml (1.84 mmol) of triethylamine are added and the mixture is stirred at RT for 2 h. 5 ml of water are added, the reaction mixture is stirred at 0° C. for 30 min and the precipitate is then filtered off with suction and dried under reduced pressure.

Yield: 321 mg (88% of theory)

LC-MS (Method 3): $R_t$=2.25 min.; MS (ESI$^+$): m/z=119 (M$^+$)

$^1$H-NMR (300 MHz, DMSO-d$_6$): δ=8.29 (d, 1H), 7.31 (d, 1H), 4.27 (q, 2H), 3.92 (s, 3H), 1.30 (t, 3H).

Example 4A

Ethyl 1-methyl-4-[({[4-(trifluoromethoxy)phenyl]amino}carbonyl)amino]-1H-pyrrole-2-carboxylate

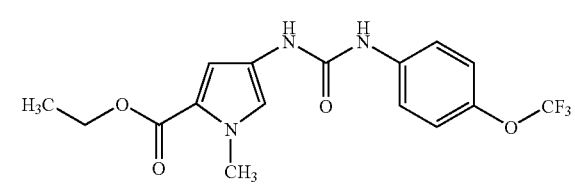 [SMILES: CCOC(=O)c1cc(NC(=O)Nc2ccc(OC(F)(F)F)cc2)cn1C]

304 mg (1.53 mmol) of ethyl 1-methyl-4-nitro-1H-pyrrole-2-carboxylate are initially charged in 6 ml of ethyl acetate/ethanol (1:1), 163 mg (0.15 mmol) of palladium (10% on activated carbon) and 580 mg (9.20 mmol) of ammonium formate are added, and the mixture is stirred at 80° C. for 1 h. After cooling, the mixture is filtered through kieselguhr, the filtercake is rinsed with ethanol and the filtrate is freed from the solvent under reduced pressure. The residue is dissolved in 6 ml of THF, 374 mg (1.84 mmol) of 4-trifluoromethoxyphenyl isocyanate are added and the mixture is stirred at RT for 1 h. The reaction solution is concentrated and the residue is purified by RP-HPLC (acetonitrile/water). This gives a solid.

Yield: 486 mg (85% of theory)

LC-MS (Method 3): $R_t$=2.61 min.; MS (ESI$^+$): m/z=372 (M+H)$^+$ $^1$H-NMR (300 MHz, DMSO-d$_6$): δ=8.80 (s, 1H), 8.39 (s, 1H), 7.53 (m, 2H), 7.26 (d, 2H), 7.20 (d, 1H), 6.72 (d, 1H), 4.20 (q, 2H), 3.82 (s, 3H), 1.28 (t, 3H).

Example 5A

1-Methyl-4-[({[4-(trifluoromethoxy)phenyl)amino}carbonyl)amino]-1H-pyrrole-2-carboxylic acid

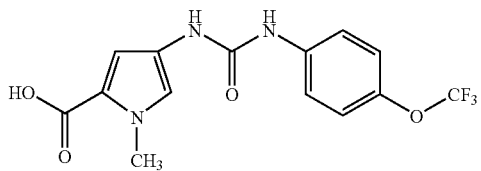 [SMILES: Cn1cc(NC(=O)Nc2ccc(OC(F)(F)F)cc2)cc1C(=O)O]

470 mg (1.27 mmol) of ethyl 1-methyl-4-[({[4-(trifluoromethoxy)phenyl]amino}carbonyl)amino]-1H-pyrrole-2-carboxylate are initially charged in 5 ml of THF, 152 mg (6.33 mmol) of lithium hydroxide in 1 ml of water are added and the mixture is stirred under reflux overnight. The reaction mixture is concentrated, the residue is acidified with 2M hydrochloric acid and the precipitate formed is filtered off with suction and dried under reduced pressure. This gives a solid.

Yield: 429 mg (98% of theory)

LC-MS (Method 2): $R_t$=2.09 min.; MS (ESI$^+$): m/z=344 (M+H)$^+$ $^1$H-NMR (300 MHz, DMSO-d$_6$): δ=12.16 (bs, 1H), 9.01 (s, 1H), 8.58 (s, 1H), 7.53 (m, 2H), 7.25 (d, 2H), 7.18 (d, 1H), 6.63 (d, 1H), 3.80 (s, 3H).

Example 6A 1-(5-Methylpyridin-2-yl)piperazine

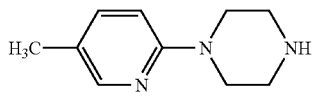

Step 1

1-(tert-Butyloxycarbonyl)-4-(5-methylpyridin-2-yl)piperazine

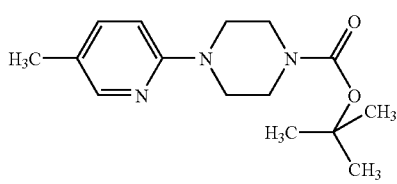 [SMILES: Cc1ccc(N2CCN(C(=O)OC(C)(C)C)CC2)nc1]

Under an atmosphere of argon, 2.50 g (19.6 mmol) of 2-methyl-5-chloropyridine and 4.38 g (23.5 mmol) of N-(tert-butyloxycarbonyl)piperazine are dissolved in 50 ml of absolute toluene. 2.26 g (23.5 mmol) of sodium tert-butoxide, 0.37 g (0.59 mmol) of BINAP and 0.36 g (0.39 mmol) of tris(dibenzylideneacetone)dipalladium are then added, and the mixture is heated at 70° C. for 12 h. After cooling, diethyl ether is added to the reaction mixture, the mixture is washed three times with saturated sodium chloride solution and dried over sodium sulphate and the solvent is removed under reduced pressure. The residue is purified by flash chromatography (cyclohexane/ethyl acetate 9:1).

Yield: 5.27 g (97% of theory).

LC-MS (Method 1): $R_t$=1.26 min.; MS (ESI$^+$): m/z=278 (M+H)$^+$ $^1$H-NMR (300 MHz, CDCl$_3$): δ=8.02 (d, 1H), 7.34 (dd, 1H), 6.59 (d, 1H), 3.55 (m, 4H), 3.45 (m, 4H), 2.21 (s, 3H), 1.49 (s, 9H).

Step 2

1-(5-Methylpyridin-2-yl)piperazine

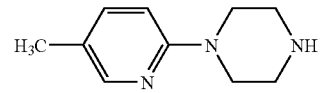

3.47 g (12.5 mmol) of 1-(tert-butyloxycarbonyl)-4-(5-methylpyridin-2-yl)piperazine are dissolved in 10 ml of dioxane, and 31 ml (125 mmol) of hydrogen chloride in dioxane (4 molar) are added. The mixture is stirred at RT for 2 h. The mixture is then concentrated and the residue is made alkaline using 1M aqueous sodium hydroxide solution and extracted repeatedly with dichloromethane. The combined organic phases are dried over sodium sulphate, concentrated and dried under reduced pressure.

Yield: 2.18 g (98% of theory).

LC-MS (Method 3): $R_t$=0.38 min.; MS (ESI$^+$): m/z=177 (M+H)$^+$ $^1$H-NMR (300 MHz, CDCl$_3$): δ=8.02 (d, 1H), 7.32 (dd, 1H), 6.59 (d, 1H), 3.45 (m, 4H), 3.00 (m, 4H), 2.20 (s, 3H).

Example 7A

1-Ethyl-4-[({[4-(trifluoromethoxy)phenyl]amino}carbonyl)amino]-1H-pyrrole-2-carboxylic acid

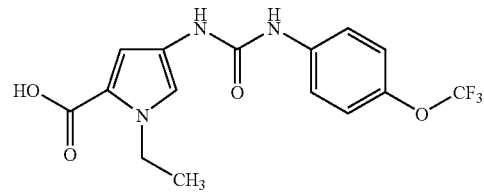 [SMILES: CCn1cc(NC(=O)Nc2ccc(OC(F)(F)F)cc2)cc1C(=O)O]

The preparation is carried out analogously to Example 5A.
LC-MS (Method 2): $R_t$=2.10 min.; MS (ESI$^+$): m/z=358 (M+H)$^+$

Example 8A

1-Butyl 4-[({[4-(trifluoromethoxy)phenyl]amino}carbonyl)amino]-1H-pyrrole-2-carboxylic acid

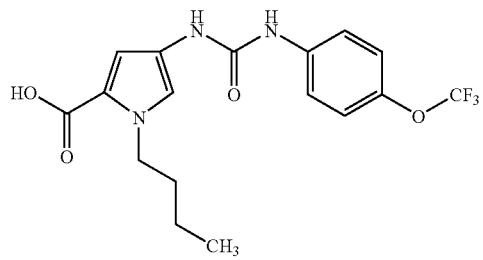

The preparation is carried out analogously to Example 5A.
LC-MS (Method 3): $R_t$=2.47 min.; MS (ESI$^+$): m/z=386 (M+H)$^+$
$^1$H-NMR (300 MHz, DMSO-d$_6$): δ=8.90 (bs, 1H), 8.48 (bs, 1H), 7.54 (d, 2H), 7.26 (d, 2H), 7.24 (d, 1H), 6.73 (d, 1H), 4.21 (t, 2H), 1.62 (quintet, 2H), 1.25 (sextet, 2H), 0.88 (t, 3H).

Example 9A 1-(Cyclopropylmethyl)-4-[({[4-(trifluoromethoxy)phenyl)amino}carbonyl)amino]-1H-pyrrole-2-carboxylic acid

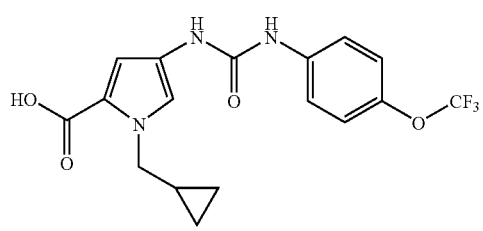 [SMILES: O=C(Nc1ccc(OC(F)(F)F)cc1)Nc1cc(C(=O)O)n(CC2CC2)c1]

The preparation was carried out analogously to Example 5A.
LC-MS (Method 2): $R_t$=2.33 min.; MS (ESI$^+$): m/z=384 (M+H)$^+$
$^1$H-NMR (300 MHz, DMSO-d$_6$)1 δ=8.86 (bs, 1H), 8.45 (bs, 1H), 7.55 (m, 2H), 7.23-7.32 (m, 3H), 6.68 (d, 1H), 4.11 (d, 2H), 1.21 (m, 1H), 0.45 (m, 2H), 0.32 (m, 2H).

Example 10A

4-[({[4-(Trifluoromethoxy)phenyl)amino}carbonyl)amino]thiophene-2-carboxylic acid

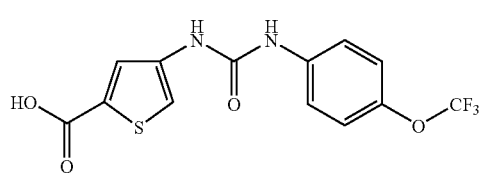 [SMILES: O=C(Nc1ccc(OC(F)(F)F)cc1)Nc1csc(C(=O)O)c1]

The preparation was carried out analogously to Examples 4A and 5A starting with methyl 4-aminothiophene-2-carboxylate (synthesized according to A. A. Kiryano et al., *Tetrahedron Lett*. 2001, (42), 8797-8800).

Yield: 72 mg (27% of theory, 2 steps)
LC-MS (Method 2): $R_t$=2.25 min.; MS (ESI$^+$): m/z=347 (M+H)$^+$
$^1$H-NMR (400 MHz, DMSO-d$_6$): δ=13.1 (bs, 1H), 9.10 (bs, 1H), 8.98 (bs, 1H), 7.69 (s, 1H), 7.53-7.60 (m, 3H), 7.29 (d, 2H).

Example 11A

2-[({[4-(Trifluoromethoxy)phenyl]amino}carbonyl)amino]-1,3-thiazole-4-carboxylic acid

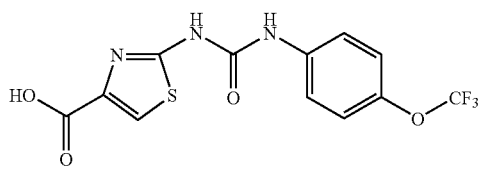 [SMILES: O=C(Nc1ccc(OC(F)(F)F)cc1)Nc1nc(C(=O)O)cs1]

The preparation was carried out analogously to Examples 4A and 5A starting with ethyl 2-amino-1,3-thiazole-4-carboxylate (commercially available from ACROS).

Yield: 290 mg (61% of theory, 2 steps)
LC-MS (Method 2): $R_t$=2.05 min.; MS (ESI$^+$): m/z=348 (M+H)$^+$
$^1$H-NMR (300 MHz, DMSO-d$_6$): δ=12.8 (bs, 1H), 10.9 (bs, 1H), 9.22 (bs, 1H), 7.91 (s, 1H), 7.60 (d, 2H), 7.32 (d, 2H).

Example 12A

5-Methyl-2-[({[4-(trifluoromethoxy)phenyl]amino}carbonyl)amino]-1,3-thiazole-4-carboxylic acid

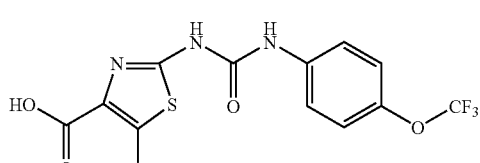

The preparation was carried out analogously to Examples 4A and 5A starting with methyl 2-amino-5-methyl-1,3-thiazole-4-carboxylate (commercially available from Tyger Scientific).

Yield: 148 mg (40% of theory, 2 steps)
LC-MS (Method 3): $R_t$=2.47 min.; MS (ESI$^+$): m/z=362 (M+H)$^+$ ¹H-NMR (300 MHz, DMSO-d₆): δ=12.7 (bs, 1H), 10.7 (bs, 1H), 9.18 (bs, 1H), 7.59 (d, 2H), 7.32 (d, 2H), 3.34 (s, 3H).

Example 13A

5-Chloro-2-[({[4-(trifluoromethoxy)phenyl]amino}carbonyl)amino]-1,3-thiazole-4-carboxylic acid

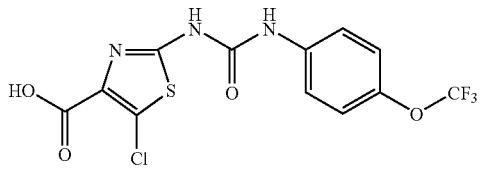

The preparation was carried out analogously to Examples 4A and 5A starting with ethyl 2-amino-5-chloro-1,3-thiazole-4-carboxylate (synthesis described in K. J. Hodgetts et al., *Org. Lett.* 2002, (4), 1363-1366).

Yield: 365 mg (89% of theory, 2 steps)
LC-MS (Method 3): R_f=2.51 min.; MS (ESI⁺): m/z=382 (M+H)⁺
¹H-NMR (300 MHz, DMSO-d₆): δ=13.2 (bs, 1H), 11.2 (bs, 1H), 9.28 (bs, 1H), 7.58 (m, 2H), 7.33 (m, 2H).

Example 14A

5-Bromo-2-[({[4-(trifluoromethoxy)phenyl]amino}carbonyl)amino]-1,3-thiazole-4-carboxylic acid

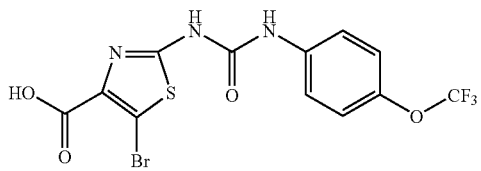

The preparation was carried out analogously to Examples 4A and 5A from ethyl 2-amino-5-bromo-1,3-thiazole-4-carboxylate (synthesis described in J. F. Okonya et al., *Tetrahedron Lett.*, 2002, (43), 7051-7054).

Yield: 343 mg (74% of theory, 2 steps)
LC-MS (Method 2): R_f=2.22 min.; MS (ESI⁺): m/z=426 (M+H)⁺
¹H-NMR (300 MHz, DMSO-d₆): δ=13.1 (bs, 1H), 11.2 (bs, 1H), 9.28 (bs, 1H), 7.58 (m, 2H), 7.32 (m, 2H).

Example 15A

2-[({[4-(Trifluoromethoxy)phenyl]amino}carbonyl)amino]-1,3-thiazole-5-carboxylic acid

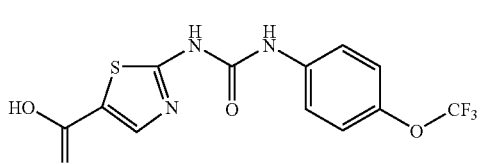

The preparation was carried out analogously to Examples 4A and 5A starting with ethyl 2-amino-1,3-thiazole-5-carboxylate (commercially available from Rare Chem).

Yield: 200 mg (55% of theory, 2 steps)
LC-MS (Method 3): R_f=2.36 min.; MS (ESI⁺): m/z=348 (M+H)⁺
¹H-NMR (300 MHz, DMSO-d₆): δ=12.8 (bs, 1H), 10.9 (bs, 1H), 9.21 (bs, 1H), 7.92 (s, 1H), 7.60 (d, 2H), 7.33 (d, 2H).

WORKING EXAMPLES

Example 1

N-{1-Methyl-5-[(4-pyridin-2-ylpiperazin-1-yl)carbonyl]-1H-pyrrol-3-yl}-N'-[4-(trifluoromethoxy)-phenyl]urea

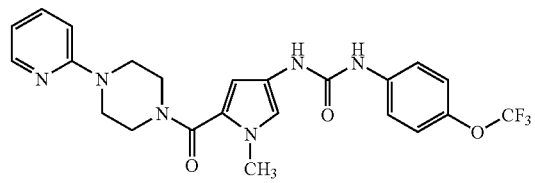 [SMILES: Cn1cc(NC(=O)Nc2ccc(OC(F)(F)F)cc2)cc1C(=O)N1CCN(c2ccccn2)CC1]

50 mg (0.15 mmol) of 1-methyl-4[({[4-(trifluoromethoxy)phenyl]amino}carbonyl)amino]-1H-pyrrole-2-carboxylic acid (Example 5A) are initially charged in 1 ml of DMF, and 56 mg (0.18 mmol) of O-(benzotriazol-1-yl)-N,N,N',N'-tetramethyluronium tetrafluoroborate (TBTU) and 8.9 mg (0.07 mmol) of 4-(dimethylamino)pyridine (DMAP) are added. 29 mg (0.18 mmol) of 1-(2-pyridyl)piperazine are then added, and the mixture is stirred at RT for 8 h. The reaction solution is purified by RP-HPLC (acetonitrile/water). This gives a solid.

Yield: 54 mg (76% of theory)
LC-MS (Method 1): R_f=1.61 min.; MS (ESI⁺): m/z=489 (M+H)⁺
¹H-NMR (300 MHz, DMSO-d₆): δ=8.75 (s, 1H), 8.32 (s, 1H), 8.13 (dd, 1H), 7.50-7.59 (m, 3H), 7.25 (d, 2H), 7.02 (d, 1H), 6.86 (d, 1H), 6.68 (dd, 1H), 6.28 (d, 1H), 3.72 (m, 4H), 3.64 (s, 3H), 3.55 (m, 4H).

Example 2

N-(1-Methyl-5-{[4-(5-methylpyridin-2-yl)piperazin-1-yl]carbonyl}-1H-pyrrol-3-yl)-N'-[4-trifluoromethoxy)phenyl]urea

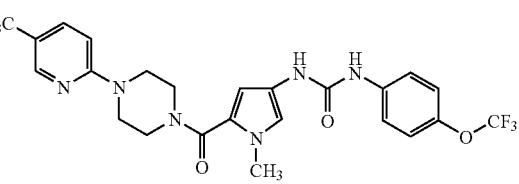

The preparation is carried out analogously to Example 1 using Examples 5A and 6A.

Yield: 50 mg (68% of theory)
LC-MS (Method 1): R_f=1.66 min.; MS (ESI⁺): m/z=503 (M+H)⁺

$^1$H-NMR (300 MHz, DMSO-d$_6$): δ=8.75 (bs, 1H), 8.32 (bs, 1H), 7.98 (d, 1H), 7.53 (m, 2H), 7.42 (dd, 1H), 7.25 (d, 2H), 7.02 (d, 1H), 6.80 (d, 1H), 6.28 (d, 1H), 3.68-3.76 (m, 4H), 3.63 (s, 3H), 3.45-3.53 (m, 4H), 2.17 (s, 3H).

Example 3

N-{1-Ethyl-[(4-pyridin-2-ylpiperazin-1-yl)carbonyl]-1H-pyrrol-3-yl}-N'-[4-(trifluoromethoxy)-phenyl]urea

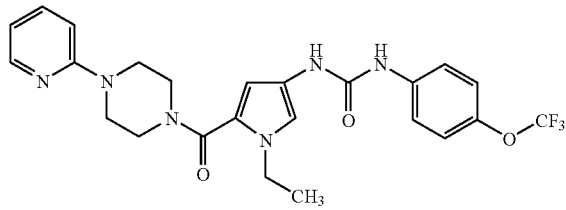 [SMILES: CCn1cc(NC(=O)Nc2ccc(OC(F)(F)F)cc2)cc1C(=O)N1CCN(c2ccccn2)CC1]

The preparation is carried out analogously to Example 1 using Examples 7A and 6A.
Yield: 29 mg (43% of theory)
LC-MS (Method 2): R$_t$=1.79 min.; MS (ESI$^+$): m/z=503 (M+H)$^+$
$^1$H-NMR (400 MHz, DMSO-d$_6$): δ=8.74 (bs, 1H), 8.32 (bs, 1H), 8.13 (d, 1H), 7.49-7.60 (m, 3H), 7.22-7.28 (m, 2H), 7.08 (s, 1H), 6.87 (d, 1H), 6.68 (dd, 1H), 6.26 (s, 1H), 4.04 (q, 2H), 3.68-3.77 (m, 4H), 3.50-3.58 (m, 4H), 1.26 (t, 3H).

Example 4

N-(1-Ethyl-5-{[4-(5-methylpyridin-2-yl)piperazin-1-yl]carbonyl}-1H-pyrrol-3-yl)-N'-[4-(trifluoromethoxy)phenyl]urea

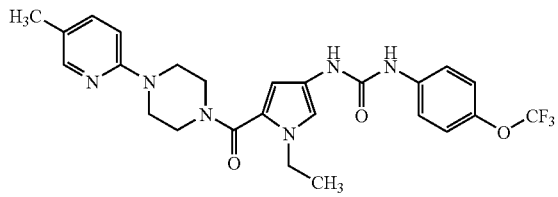 [SMILES: CCn1cc(NC(=O)Nc2ccc(OC(F)(F)F)cc2)cc1C(=O)N1CCN(c2ccc(C)cn2)CC1]

The preparation is carried out analogously to Example 1 using Examples 7A and 6A.
Yield: 26 mg (39% of theory)
LC-MS (Method 2): R$_t$=1.80 min.; MS (ESI$^+$): m/z=517 (M+H)$^+$
$^1$H-NMR (400 MHz, DMSO-d$_6$): δ=8.75 (bs, 1H), 8.32 (bs, 1H), 7.98 (m, 1H), 7.54 (m, 2H), 7.42 (m, 1H), 7.26 (m, 2H), 7.08 (m, 1H), 6.80 (d, 1H), 6.25 (s, 1H), 4.03 (q, 2H), 3.68-3.76 (m, 4H), 3.44-3.52 (m, 4H), 2.18 (s, 3H), 1.25 (t, 3H).

Example 5

N-{1-Butyl-5-[(4-pyridin-2-ylpiperazin-1-yl)carbonyl]-1H-pyrrol-3-yl}-N'[4-(trifluoromethoxy)-phenyl]urea

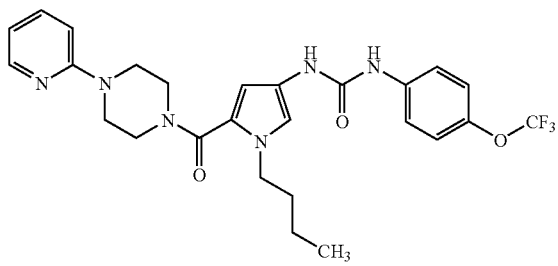 [SMILES: CCCCn1cc(NC(=O)Nc2ccc(OC(F)(F)F)cc2)cc1C(=O)N1CCN(c2ccccn2)CC1]

The preparation is carried out analogously to Example 1 using Example 8A.
Yield: 41 mg (69% of theory)
LC-MS (Method 2): R$_t$=2.11 min.; MS (ESI$^+$): m/z=531 (M+H)$^+$
$^1$H-NMR (400 MHz, DMSO-d$_6$): δ=8.75 (bs, 1H), 8.33 (bs, 1H), 8.12 (d, 1H), 7.58 (m, 1H), 7.54 (d, 2H), 7.26 (d, 2H), 7.07 (d, 1H), 6.87 (d, 1H), 6.68 (dd, 1H), 6.26 (d, 1H), 4.02 (t, 2H), 3.72 (m, 4H), 3.53 (m, 4H), 1.59 (quint., 2H), 1.18 (sext., 2H), 0.84 (t, 3H).

Example 6

N-(1-Butyl-5-{[4-(5-methylpyridin-2-yl)piperazin-1-yl]carbonyl}-1H-pyrrol-3-yl)-N'-[4-(trifluoromethoxy)phenyl]urea

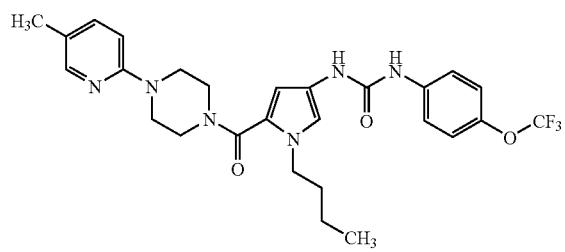 [SMILES: CCCCn1cc(NC(=O)Nc2ccc(OC(F)(F)F)cc2)cc1C(=O)N1CCN(c2ccc(C)cn2)CC1]

The preparation is carried out analogously to Example 1 using Examples 8A and 6A.
Yield: 19 mg (20% of theory)
LC-MS (Method 2): R$_t$=1.97 min.; MS (ESI$^+$): m/z=545 (M+H)$^+$
$^1$H-NMR (300 MHz, DMSO-d$_6$): δ=8.74 (bs, 1H), 8.32 (bs, 1H), 7.98 (d, 1H), 7.53 (d, 2H), 7.41 (dd, 1H), 7.25 (d, 2H), 7.07 (d, 1H), 6.80 (d, 1H), 6.25 (d, 1H), 4.02 (t, 2H), 3.72 (m, 4H), 3.47 (m, 4H), 2.16 (s, 3H), 1.59 (quint, 2H), 1.18 (next., 2H), 0.83 (t, 3H).

Example 7

N-{1-(Cyclopropylmethyl)-5-[(4-pyridin-2-ylpiperazin-1-yl)carbonyl]-1H-pyrrol-3-yl}-N'-[4-(trifluoromethoxy)phenyl]urea

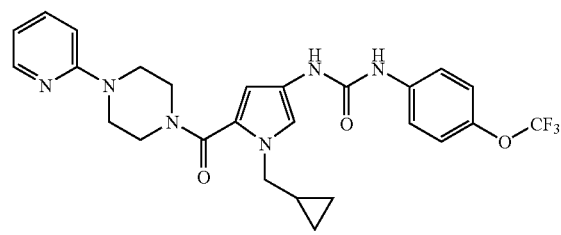 [SMILES: O=C(Nc1ccc(OC(F)(F)F)cc1)Nc1cc(C(=O)N2CCN(c3ccccn3)CC2)n(CC2CC2)c1]

The preparation is carried out analogously to Example 1 using Example 9A.
Yield: 51 mg (86% of theory)
LC-MS (Method 1): R$_t$=1.84 min.; MS (ESI$^+$): m/z=529 (M+H)$^+$
$^1$H-NMR (300 MHz, DMSO-d$_6$): δ=8.75 (bs, 1H), 8.33 (bs, 1H), 8.13 (dt, 1H), 7.51-7.61 (m, 3H), 7.27 (d, 2H), 7.13 (d, 1H), 6.88 (d, 1H), 6.69 (dd, 1H), 6.28 (d, 1H), 3.90 (d, 2H), 3.73 (m, 4H), 3.53 (m, 4H), 1.12 (m, 1H), 0.45 (m, 2H), 0.28 (m, 2H).

Example 8

N-(1-(Cyclopropylmethyl)-5-{[4-(5-methylpyridin-2-yl)piperazin-1-yl]carbonyl}-1H-pyrrol-3-yl)-N'-[4-(trifluoromethoxy)phenyl]urea

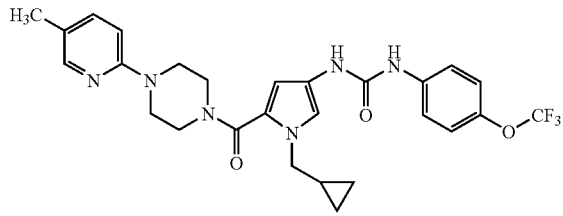 [SMILES: Cc1ccc(N2CCN(C(=O)c3cc(NC(=O)Nc4ccc(OC(F)(F)F)cc4)cn3CC3CC3)CC2)nc1]

The preparation is carried out analogously to Example 1 using Examples 9A and 6A.

Yield: 52 mg (85% of theory)

LC-MS (Method 1): δ=1.86 min.; MS (ESI⁺): m/z=543 (M+H)⁺

¹H-NMR (300 MHz, DMSO-d₆): δ=8.77 (bs, 1H), 8.34 (bs, 1H), 7.98 (d, 1H), 7.54 (d, 2H), 7.41 (dd, 1H), 7.25 (d, 2H), 7.12 (d, 1H), 6.80 (d, 1H), 6.27 (d, 1H), 3.89 (d, 2H), 3.72 (m, 4H), 3.48 (m, 4H), 2.16 (s, 3H), 1.12 (m, 1H), 0.45 (m, 2H), 0.28 (m, 2H).

Example 9

N-(5-{[4-(5-Methylpyridin-2-yl)piperazin-1-yl]carbonyl}-3-thienyl)-N'-[4-(trifluoromethoxy)phenyl]urea

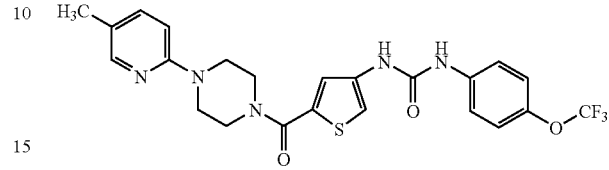

The preparation is carried out analogously to Example 1 using Examples 10A and 6A.

Yield: 60 mg (63% of theory)

LC-MS (Method 3): R$_t$=2.05 min.; MS (ESI⁺): m/z=506 (M+H)⁺

¹H-NMR (400 MHz, DMSO-d₆): δ=9.05 (bs, 1H), 8.95 (bs, 1H), 7.98 (d, 1H), 7.56 (d, 2H), 7.47 (s, 1H), 7.39-7.44 (m, 2H), 7.29 (d, 2H), 6.80 (d, 1H), 3.75 (m, 4H), 3.51 (m, 4H), 2.16 (s, 3H).

The following compounds are synthesized analogously to Example 1 from the appropriate starting materials:

| Ex. No. | Structure | Starting material | Yield | LC-MS R$_t$ [min] | MS (M + H)⁺ |
|---|---|---|---|---|---|
| 10 | 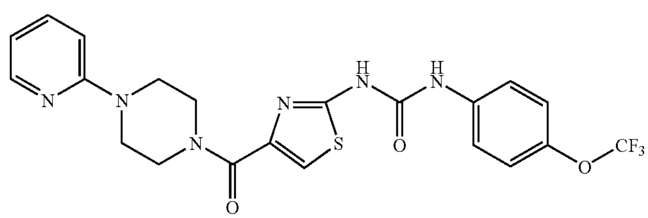 [SMILES: O=C(Nc1ccc(OC(F)(F)F)cc1)Nc1nc(C(=O)N2CCN(c3ccccn3)CC2)cs1] | Example 11A | 36 mg (51% of theory) | 1.95 (Method 3) | 493 |
| 11 | 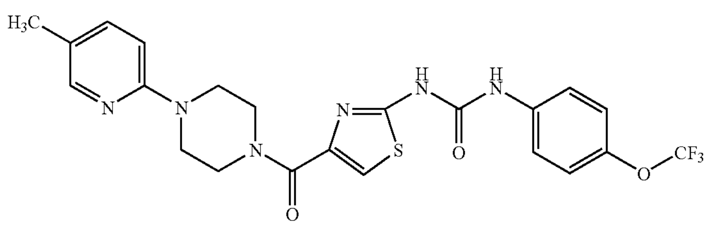 [SMILES: Cc1ccc(N2CCN(C(=O)c3csc(NC(=O)Nc4ccc(OC(F)(F)F)cc4)n3)CC2)nc1] | Example 11A | 49 mg (67% of theory) | 2.02 (Method 3) | 507 |
| 12 | 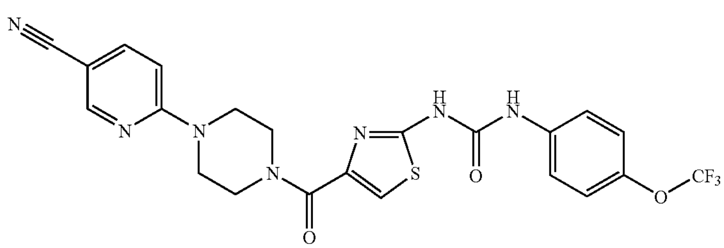 [SMILES: N#Cc1ccc(N2CCN(C(=O)c3csc(NC(=O)Nc4ccc(OC(F)(F)F)cc4)n3)CC2)nc1] | Example 11A | 43 mg (58% of theory) | 2.52 (Method 3) | 518 |

| Ex. No. | Structure | Starting material | Yield | LC-MS R<sub>t</sub> [min] | MS (M + H)⁺ |
|---|---|---|---|---|---|
| 13 | 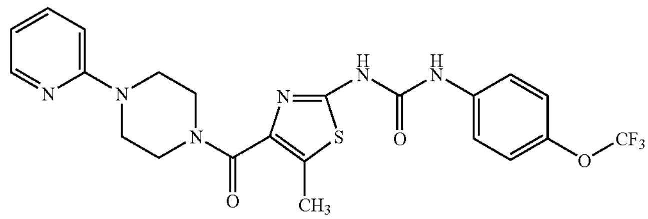 [SMILES: Cc1sc(NC(=O)Nc2ccc(OC(F)(F)F)cc2)nc1C(=O)N1CCN(c2ccccn2)CC1] | Example 12A | 33 mg (48% of theory) | 2.00 (Method 3) | 507 |
| 14 | 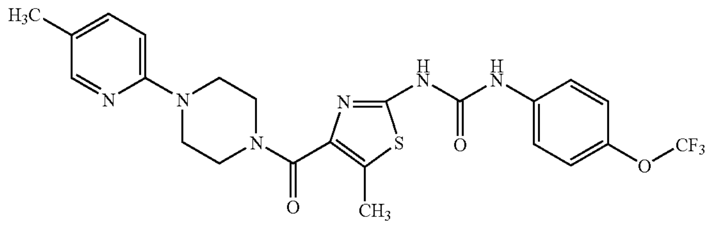 [SMILES: Cc1ccc(N2CCN(C(=O)c3nc(NC(=O)Nc4ccc(OC(F)(F)F)cc4)sc3C)CC2)nc1] | Example 12A | 50 mg (70% of theory) | 2.01 (Method 3) | 521 |
| 15 | 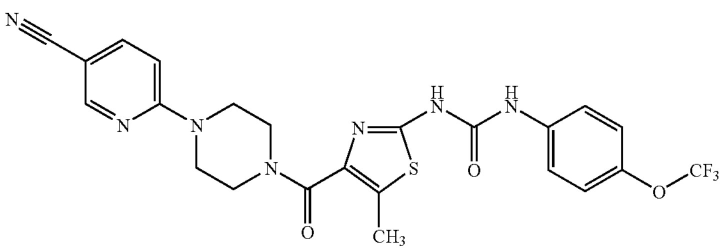 [SMILES: Cc1sc(NC(=O)Nc2ccc(OC(F)(F)F)cc2)nc1C(=O)N1CCN(c2ccc(C#N)cn2)CC1] | Example 12A | 52 mg (71% of theory) | 2.60 (Method 3) | 532 |
| 16 | 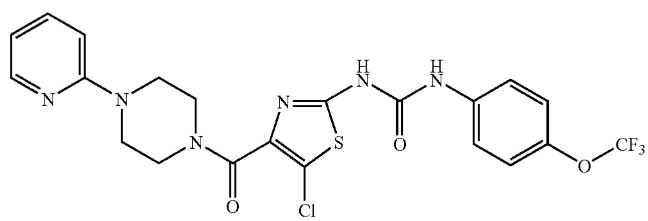 [SMILES: O=C(Nc1ccc(OC(F)(F)F)cc1)Nc1nc(C(=O)N2CCN(c3ccccn3)CC2)c(Cl)s1] | Example 13A | 43 mg (58% of theory) | 2.21 (Method 3) | 527 |
| 17 | 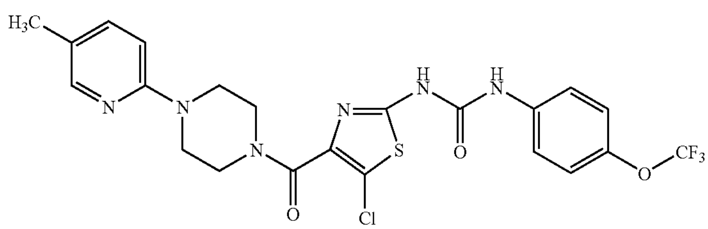 [SMILES: Cc1ccc(N2CCN(C(=O)c3nc(NC(=O)Nc4ccc(OC(F)(F)F)cc4)sc3Cl)CC2)nc1] | Example 13A | 35 mg (49% of theory) | 2.24 (Method 3) | 541 |
| 18 | 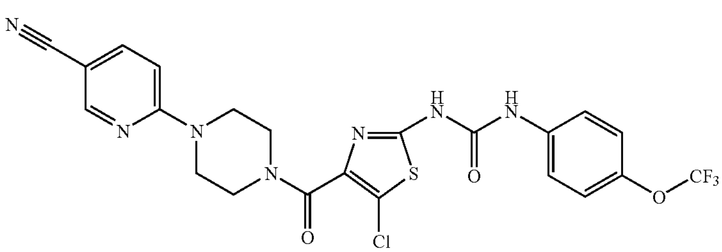 [SMILES: N#Cc1ccc(N2CCN(C(=O)c3nc(NC(=O)Nc4ccc(OC(F)(F)F)cc4)sc3Cl)CC2)nc1] | Example 13A | 42 mg (52% of theory) | 2.76 (Method 3) | 552 |

-continued

| Ex. No. | Structure | Starting material | Yield | LC-MS R$_t$ [min] | MS (M + H)$^+$ |
|---|---|---|---|---|---|
| 19 | 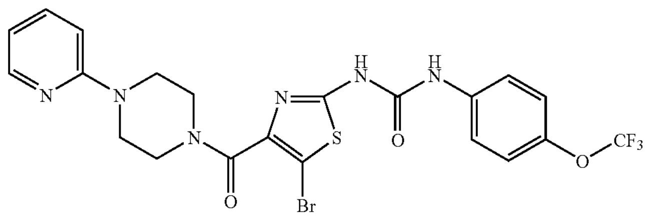 | Example 14A | 45 mg (59% of theory) | 2.22 (Method 3) | 571 |
| 20 | 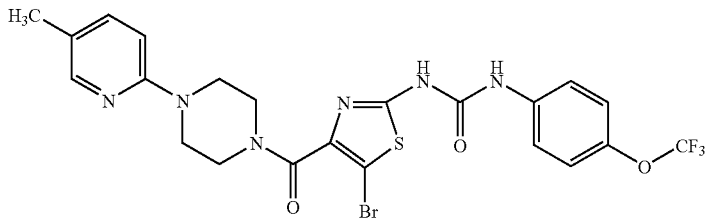 | Example 14A | 50 mg (68% of theory) | 2.27 (Method 3) | 585 |
| 21 | 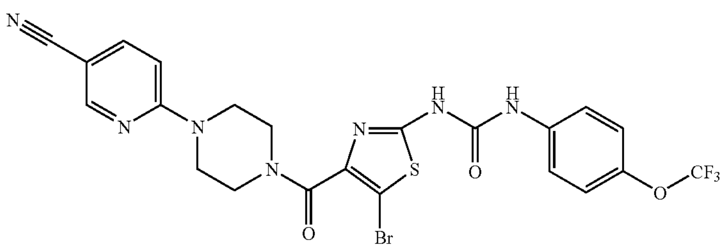 [SMILES: N#Cc1ccc(N2CCN(C(=O)c3nc(NC(=O)Nc4ccc(OC(F)(F)F)cc4)sc3Br)CC2)nc1] | Example 14A | 41 mg (50% of theory) | 2.77 (Method 3) | 596 |
| 22 | 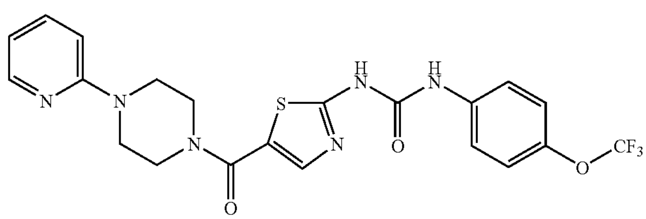 [SMILES: O=C(Nc1ccc(OC(F)(F)F)cc1)Nc1ncc(C(=O)N2CCN(c3ccccn3)CC2)s1] | Example 15A | 34 mg (49% of theory) | 1.90 (Method 3) | 493 |
| 23 | 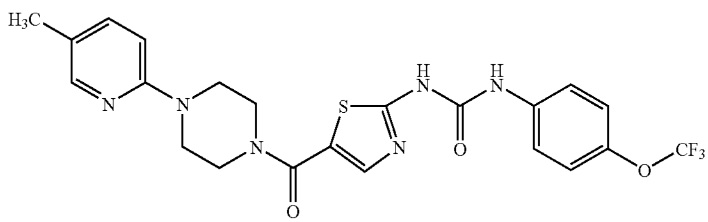 [SMILES: Cc1ccc(N2CCN(C(=O)c3cnc(NC(=O)Nc4ccc(OC(F)(F)F)cc4)s3)CC2)nc1] | Example 15A | 47 mg (65% of theory) | 1.93 (Method 3) | 507 |
| 24 | 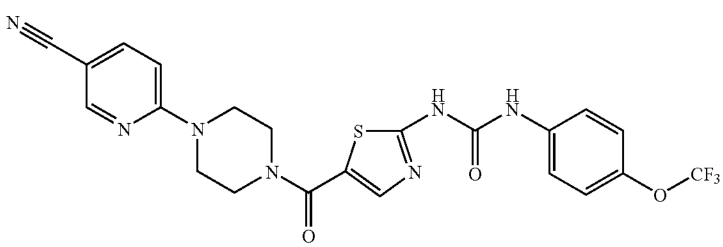 [SMILES: N#Cc1ccc(N2CCN(C(=O)c3cnc(NC(=O)Nc4ccc(OC(F)(F)F)cc4)s3)CC2)nc1] | Example 15A | 47 mg (64% of theory) | 2.53 (Method 3) | 518 |

B. ASSESSMENT OF THE PHYSIOLOGICAL ACTIVITY

The in vitro effect of the compounds of the invention can be shown in the following assays:

Anti-HCMV (Anti-Human Cytomegalovirus) Cytopathogenicity Tests

The test compounds are employed as 50 millimolar (mM) solutions in dimethyl sulphoxide (DMSO). Ganciclovir, foscarnet and cidofovir are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. Then 150 µl portions of a suspension of $1 \times 10^4$ cells (human prepuce fibroblasts [NHDF]) are pipetted into each of the wells (row 1=cell control) and, in rows 2-12, a mixture of HCMV-infected and uninfected NHDF cells (M.O.I.=0.001–0.002), i.e. 1-2 infected cells per 1000 uninfected cells. Row 12 (without substance) serves as virus control. The final test concentrations are 250-0.0005 µM. The plates are incubated at 37° C./5% $CO_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (Plaque Multiplier from Technomara).

The following data can be acquired from the test plates:

$CC_{50}$ (NHDF)=maximum substance concentration in µM at which no visible cytostatic effects on the cells are evident by comparison with the untreated cell control;

$EC_{50}$ (HCMV)=substance concentration in µM which inhibits the CPE (cytopathic effect) by 50% compared with the untreated virus control;

SI (selectivity index)=$CC_{50}$ (NHDF)/$EC_{50}$ (HCMV).

Representative in vitro data for the effects of the compounds of the invention are shown in Table A:

TABLE A

| Example No. | NHDF $CC_{50}$ [µM] | HCMV $EC_{50}$ [µM] | SI HCMV |
|---|---|---|---|
| 4 | 21 | 0.0007 | 28767 |
| 9 | 21 | 0.0059 | 3559 |
| 14 | 11 | 0.0016 | 7333 |
| 23 | 11 | 0.0054 | 2637 |

The suitability of the compounds of the invention for the treatment of HCMV infections can be shown in the following animal model:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Bomholtgaard, Jackson). The animals are housed under sterile conditions (including bedding and feed) in isolators.

Virus Growing:

Human cytomegalovirus (HCMV), Davis strain, is grown in vitro on human embryonic prepuce fibroblasts (NHDF cells). After the NHDF cells have been infected with a multiplicity of infection (M.O.I.) of 0.01, the virus-infected cells are harvested 5-7 days later and stored in the presence of minimal essential medium (MEM), 10% foetal calf serum (FCS) with 10% DMSO at −40° C. After serial ten-fold dilutions of the virus-infected cells, the titre is determined on 24-well plates of confluent NHDF cells after vital staining with Neutral Red, or fixation and staining with a formalin/Giemsa mixture (as described above).

Preparation of the Sponges, Transplantation, Treatment and Evaluation:

Collagen sponges 1×1×1 cm in size (Gelfoam®; from Peasel & Lorey, order No. 407534; K. T. Chong et al., Abstracts of 39th Interscience Conference on Antimicrobial Agents and Chemotherapy, 1999, p. 439; P. M. Kraemer et al., Cancer Research 1983, (43): 4822-4827) are initially wetted with phosphate-buffered saline (PBS), the trapped air bubbles are removed by degassing, and then stored in MEM+10% FCS. $1 \times 10^6$ virus-infected NHDF cells (infection with HCMV Davis M.O.I.=0.01) are detached 3 hours after infection and added in a drop of 20 µl of MEM, 10% of FCS, to a moist sponge. 12-13 hours later, the infected sponges are optionally incubated for 1 hour with 25 µl of PBS/0.1% BSA/1 mM DTT with 5 ng/µl basic fibroblast growth factor (bFGF). For the transplantation, the immunodeficient mice are anaesthetized with avertin or a mixture of xylazine/azepromazine and ketamine, the fur on the back is removed using a shaver, the epidermis is opened 1-2 cm, unstressed and the moist sponges are transplanted under the dorsal skin. The surgical wound is closed with tissue glue. 24 hours after the transplantation, the mice are, over a period of 8 days, treated with substance perorally three times a day (7.00 h and 14.00 h and 19.00 h), two times a day (8.00 h and 17.00 h) or once a day (14.00 h). The dose is 3 or 10 or 30 or 100 mg/kg of body weight, the volume administered is 10 ml/kg of body weight. The substances are formulated in the form of a 0.5% strength Tylose suspension, optionally with 2% DMSO. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% foetal calf serum, 10% DMSO at −140° C. Evaluation takes place after serial ten-fold dilutions of the virus-infected cells by determining the titre on 24-well plates of confluent NHDF cells after vital staining with Neutral Red or after fixation and staining with a formalin/Giemsa mixture (as described above). The number of infectious virus particles after the substance treatment compared with the placebo-treated control group is determined.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of active compound, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:
Composition:
1000 mg of the compound of Example 1, 1000 mg of ethanol (96%), 400 mg of Rhodigel (xanthan gum from FMC, Pennsylvania, USA) and 99 g of water.
10 ml of oral suspension are equivalent to a single dose of 100 mg of the compound of the invention.
Production:
The Rhodigel is suspended in ethanol, and the active compound is added to the suspension. The water is added while stirring. The mixture is stirred for about 6 h until the swelling of the Rhodigel is complete.
Solution which can be Administered Intravenously:
Composition:
1 mg of the compound of Example 1, 15 g of polyethylene glycol 400 and 250 g of water for injection purposes.
Production:
The compound of the invention is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and crimp caps.

The invention claimed is:
1. A compound of the formula

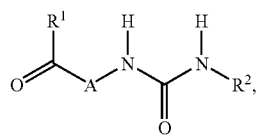
(I)

in which
$R^1$ represents a group of the formula

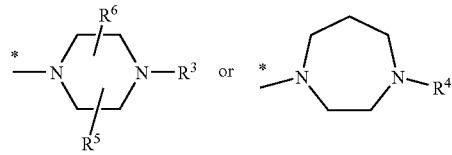

where
* represents the point of attachment to the carbonyl group,
$R^3$ represents phenyl or 5- or 6-membered heteroaryl,
where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
$R^4$ represents phenyl or 5- or 6-membered heteroaryl,
where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and
$R^5$ and $R^6$ independently of one another represent hydrogen, methyl or ethyl,
$R^2$ represents phenyl,
where phenyl may be substituted by 1 to 3 substituents, where the substituents independently of one another are selected from the group consisting of halogen, hydroxyl, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy,
A represents a group of the formula

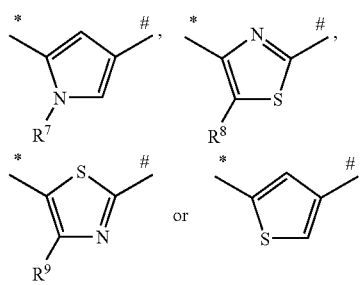

where
* represents the point of attachment to the carbonyl group,
# represents the point of attachment to the nitrogen atom of the urea,
$R^7$ represents $C_1$-$C_6$-alkyl,
where alkyl may be substituted by one substituent, where the substituent is selected from the group consisting of $C_3$-$C_6$-cycloalkyl, $C_6$-$C_{10}$-aryl and 5- or 6-membered heteroaryl,
where cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
and
$R^8$ and $R^9$ represent, independently of one another, hydrogen, halogen or $C_1$-$C_6$-alkyl,
where alkyl may be substituted by one substituent, where the substituent is selected from the group consisting of $C_3$-$C_6$-cycloalkyl, $C_6$-$C_{10}$-aryl and 5- or 6-membered heteroaryl,
in which cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, or a salt thereof.

2. The compound according to claim 1, characterized in that $R^1$ represents a group of the formula

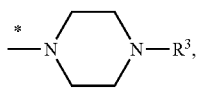

where

* represents the point of attachment to the carbonyl group, $R^3$ represents phenyl or 5- or 6-membered heteroaryl,
where phenyl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^2$ represents phenyl,
where phenyl may be substituted by 1 to 3 substituents, where the substituents independently of one another are selected from the group consisting of halogen, hydroxyl, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy, A represents a group of the formula

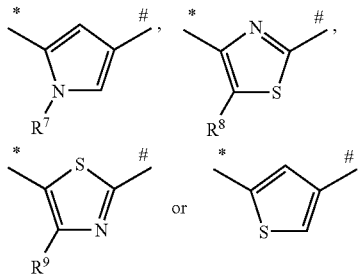

where

* represents the point of attachment to the carbonyl group, # represents the point of attachment to the nitrogen atom of the urea, $R^7$ represents $C_1$-$C_6$-alkyl,
where alkyl may be substituted by one substituent, where the substituent is selected from the group consisting of $C_3$-$C_6$-cycloalkyl, $C_6$-$C_{10}$-aryl, and 5- or 6-membered heteroaryl,
where cycloalkyl, aryl and heteroaryl may be substituted by 1 to 3 substituents, where the substituents independently of one another are selected from the group consisting of halogen, hydroxyl, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and $R^8$ and $R^9$ represent, independently of one another, hydrogen, halogen or $C_1$-$C_6$-alkyl, or a salt thereof.

3. The compound according to claim 1, characterized in that $R^1$ represents a group of the formula

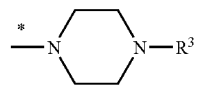

where

* represents the point of attachment to the carbonyl group, $R^3$ represents phenyl or pyridyl,
where phenyl and pyridyl may be substituted by 1 to 3 substituents, where the substituents independently of one another are selected from the group consisting of halogen, nitro, cyano, trifluoromethyl, difluoromethyl, trifluoromethoxy, difluoromethoxy, monofluoromethoxy, $C_1$-$C_4$-alkyl and $C_1$-$C_4$-alkoxy, $R^2$ represents phenyl,
where phenyl may be substituted by 1 to 3 substituents, where the substituents independently of one another are selected from the group consisting of fluorine, chlorine, trifluoromethoxy, difluoromethoxy, trifluoromethylthio and methyl, A represents a group of the formula

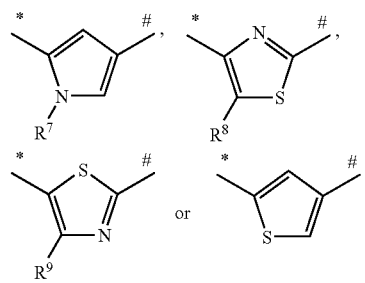

where

* represents the point of attachment to the carbonyl group, # represents the point of attachment to the nitrogen atom of the urea, $R^7$ represents methyl, ethyl or n-butyl,
where methyl, ethyl and n-butyl may be substituted by one substituent, where the substituent is selected from the group consisting of cyclopropyl and phenyl,
where phenyl may be substituted by one trifluoromethyl substituent, and $R^8$ and $R^9$ represent, independently of one another, hydrogen, bromine, chlorine, methyl or ethyl, or a salt thereof.

4. A process for preparing a compound of the formula (I) according to claim 1 or a salt thereof, characterized in that according to process (A) a compound of the formula

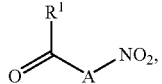 (II)

in which

R¹ is as defined in claim 1, is reacted in the first step with a reducing agent and in the second step in the presence of a carbonic acid derivative with a compound of the formula

 (III)

in which

R² is as defined in claim 1, or according to process (B) a compound of the formula (II) is reacted in the first step with a reducing agent and in the second step with a compound of the formula

 (IV), in which

R² is as defined in claim 1, or according to process (C) a compound of the formula

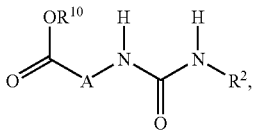 (V)

in which

R² is as defined in claim 1, and

R¹⁰ represents methyl or ethyl, is reacted in the first step with a base and in the second step with a compound of the formula

 (VI), in which

R¹ is as defined in claim 1, in the presence of a dehydrating agent.

5. A pharmaceutical composition comprising a compound according to claim 1 or a salt thereof in combination with at least one inert nontoxic, pharmaceutically acceptable auxiliary.

6. A method for controlling human cytomegalovirus (HCMV) infections in humans and animals by comprising administering an antivirally effective amount of at least one compound according to claim 1 or a salt thereof.

* * * * *